(12) United States Patent
Ayala et al.

(10) Patent No.: US 9,993,426 B2
(45) Date of Patent: Jun. 12, 2018

(54) BISACODYL COMPOSITIONS AND DELIVERY APPARATUS

(71) Applicant: C.B. FLEET COMPANY INCORPORATED, Lynchburg, VA (US)

(72) Inventors: Nelson P. Ayala, Lynchburg, VA (US); Ping Qiu, Roanoke, VA (US); Debanjan Das, Lynchburg, VA (US); Dave Zimmerman, Rustburg, VA (US)

(73) Assignee: C. B. Fleet Company, Inc., Lynchburg, VA (US)

( * ) Notice: Subject to any disclaimer, the term of this patent is extended or adjusted under 35 U.S.C. 154(b) by 0 days. days.

(21) Appl. No.: 15/258,865

(22) Filed: Sep. 7, 2016

(65) Prior Publication Data

US 2017/0079911 A1 Mar. 23, 2017

Related U.S. Application Data

(60) Provisional application No. 62/218,795, filed on Sep. 15, 2015.

(51) Int. Cl.
| | |
|---|---|
| *A61K 9/08* | (2006.01) |
| *A61K 9/02* | (2006.01) |
| *A61K 31/4402* | (2006.01) |
| *A61M 3/02* | (2006.01) |
| *B32B 1/08* | (2006.01) |
| *B32B 15/08* | (2006.01) |
| *B32B 15/20* | (2006.01) |
| *B32B 27/08* | (2006.01) |
| *B32B 27/32* | (2006.01) |
| *B65D 35/24* | (2006.01) |
| *B65D 47/12* | (2006.01) |
| *B65D 35/14* | (2006.01) |
| *A61K 9/00* | (2006.01) |
| *A61K 47/10* | (2017.01) |
| *A61K 47/32* | (2006.01) |
| *B32B 15/085* | (2006.01) |

(52) U.S. Cl.
CPC ............. *A61K 9/08* (2013.01); *A61K 9/0031* (2013.01); *A61K 9/02* (2013.01); *A61K 31/4402* (2013.01); *A61K 47/10* (2013.01); *A61K 47/32* (2013.01); *A61M 3/0262* (2013.01); *A61M 3/0279* (2013.01); *B32B 1/08* (2013.01); *B32B 15/08* (2013.01); *B32B 15/085* (2013.01); *B32B 15/20* (2013.01); *B32B 27/08* (2013.01); *B32B 27/32* (2013.01); *B65D 35/14* (2013.01); *B65D 35/24* (2013.01); *B65D 47/12* (2013.01); *B32B 2439/00* (2013.01); *B32B 2439/80* (2013.01)

(58) Field of Classification Search
None
See application file for complete search history.

(56) References Cited

U.S. PATENT DOCUMENTS

| | | | |
|---|---|---|---|
| 4,432,966 A | 2/1984 | Zeitoun et al. | |
| 4,670,419 A * | 6/1987 | Uda ....................... | A61K 47/40 514/10.1 |
| 4,910,021 A | 3/1990 | Davis et al. | |
| 5,068,110 A | 11/1991 | Fawzi et al. | |
| 5,171,580 A | 12/1992 | Iamartino et al. | |
| 5,330,759 A | 7/1994 | Pagay et al. | |
| 5,595,980 A * | 1/1997 | Brode .................. | A61K 9/0014 424/DIG. 14 |
| 5,656,290 A | 8/1997 | Kelm et al. | |
| 5,670,158 A * | 9/1997 | Davis ..................... | A61K 9/145 424/400 |
| 7,704,948 B2 | 4/2010 | Prater et al. | |
| 8,147,445 B2 * | 4/2012 | Cox .................... | A61M 3/0262 604/132 |
| 8,377,532 B2 * | 2/2013 | Maurice ................. | B29C 53/38 428/35.8 |
| 2006/0198815 A1* | 9/2006 | Barker ............. | A61K 47/48184 424/78.27 |
| 2010/0087537 A1 | 4/2010 | Venkataraman et al. | |
| 2012/0010060 A1 | 1/2012 | Fenn-Barrabass et al. | |
| 2012/0207825 A1 | 8/2012 | Roy et al. | |
| 2014/0186872 A1 | 7/2014 | Feve et al. | |
| 2015/0018778 A1 | 1/2015 | Cox | |

FOREIGN PATENT DOCUMENTS

| | | |
|---|---|---|
| WO | 1994/018973 | 9/1994 |
| WO | 1996/036321 | 11/1996 |
| WO | 1998/02148 | 1/1998 |
| WO | 2017/048566 | 3/2017 |

OTHER PUBLICATIONS

Lubrizol, "Carbopo® ETD 2020 polymer for personal care applications", Lubrizol Advanced Materials, Inc., Technical Data Sheet, TDS-187, 2 pages, (2007).
Kamm, M.A. et al., "Dynamic scanning defines a colonic defect in severe idiopathic constipation", Gut, vol. 29, pp. 1085-1092, (1988).
International Search Report and Written Opinion dated Jan. 20, 2017 for PCT application No. PCT/US2016/050570.
MedlinePlus Drug Information, "Bisacodyl" MedlinePlus 4 pages, found at www.nlm.nih./gov/medlineplus/druginfo/meds/a601027.html, (2017).
Jauch, R. et al., "Bis-(p-hydroxyphenyl)-pyridyl-2-methane: The common laxative principle of bisacodyl and sodium picosulfate", Arzneim-Forsch, Drug Research, vol. 25, No. 11, pp. 1796-1800, (1975).
Wexner, S.D. et al., "A consensus document on bowel preparation before colonoscopy: Prepared by a task force from the American Society of Colon and Rectal Surgeons (ASCRS), the American Society for Gastrointestianl Endoscopy (ASGE), and the Society of American Gastrointestinal and Endoscopic Surgeons (SAGES)", Gastrointestinal Endoscopy, vol. 63, issue 7, pp. 894-909, (2006).

(Continued)

*Primary Examiner* — Robert A Wax
*Assistant Examiner* — Quanglong N Truong

(57) ABSTRACT

A pharmaceutical composition comprising bisacodyl [4,4'-(pyridine-2-ylmethylene)bis(4,1-phenylene) diacetate], a solvent, a buffer, and a polymer, methods and apparatus for delivery to a patient.

20 Claims, 11 Drawing Sheets

(56) References Cited

OTHER PUBLICATIONS

Engelhorn, R. et al., "Laxatives", Ullmann's Encyclopedia of Industrial Chemistry, Wiley-VCH, Weinheim, pp. 541-549, (2000).
Preston, D.M. et al., "Pelvic motility and response to intraluminal bisacodyl in slow-transit constipation", Digestive Diseases and Sciences, vol. 30, issue 4, pp. 289-294, (1985).
Leng-Peschlow, E., "Effects of sennosides A+ B and bisacodyl on rat large intestine", Pharmacology, vol. 38, No. 5, pp. 310-318, (1989).
Grimm, W. et al., "Die anwendung der reaktionskinetik in der stabilitätsprüfung", Pharm. Ind., vol. 35, No. 11, pp. 733-737, (1973).
Carstensen, J.T. "Drug stability: principles and practices", Marcel Dekker, Inc., New York, Second Edition, Chapter 7, pp. 184-185, pp. 194-195, (1995).

\* cited by examiner

BISACODYL COMPOSITIONS AND DELIVERY APPARATUS

BACKGROUND OF THE INVENTION

Field of the Invention

The present invention relates to bisacodyl compositions, delivery devices, and methods of use as a rectal suppository.

Description of the Related Art

Bisacodyl (4,4'-(pyridin-2-ylmethylene)bis(4,1-phenylene) diacetate) is an organic compound used as a contact laxative drug. Bisacodyl is an inactive prodrug hydrolyzed by intestinal brush border enzymes and colonic bacteria to active desacetyl bisacodyl. Contact of the desacetyl bisacodyl with the mucosa of the colon stimulates sensory nerve endings to produce increased propulsive peristaltic contractions of the colon accelerating movement of contents through the colon. Jauch, et al., *Arzneim.-Forsch./Drug Res.* 25(11): 1796-1800, 1975. Bisacodyl is used to relieve constipation and for the management of neurogenic bowel dysfunction as well as part of bowel preparation before medical examinations, such as colonoscopy. Wexner, et al. *Gastrointestinal Endoscopy* 63 (7): 894-909; Robert Engelhorn, Ernst Seeger and Jan H. Zwaving "Laxatives" in Ullmann's Encyclopedia of Industrial Chemistry, Wiley-VCH, Weinheim, 2000.

Bisacodyl can be administered orally in a dosage range of 5-10 milligrams and takes 6-12 hours to have an effect. Bisacodyl may be administered rectally in suppository form in a dosage range of 10 mg and is usually effective in 15-60 minutes. Robert Engelhorn, Ernst Seeger and Jan H. Zwaving "Laxatives" in Ullmann's Encyclopedia of Industrial Chemistry, Wiley-VCH, Weinheim, 2000; Kamm, et al., *Gut* 29: 1085-1092, 1988; Preston & Lennard-Jones *Digestive Diseases and Sciences* 30(4): 289-294, 1985; Leng-Peschlow *Pharmacology* 38: 310-318, 1988.

Numerous compositions for oral delivery of bisacodyl are known in the art. Commercially available bisacodyl compositions for oral delivery may be coated with a low level of an enteric polymer or combination of polymers, e.g., Dulcolax® (enteric coated bisacodyl tablets) Dulcolax® is coated with a low level of cellulose acetate phthalate, and each tablet has about 5 mg of bisacodyl.

U.S. Pat. No. 5,171,580 discloses a preparation for delivery in the large intestine and especially the colon, comprising an active containing core coated with three protection layers of coatings having different solubilities. The inner layer is Eudragit® S, with a coating thickness of about 40-120 microns, the intermediate coating layer is a swellable polymer with a coating thickness of about 40-120 microns, and the outer layer is cellulose acetate phthalate, hydroxypropylmethyl cellulose phthalate, polyvinyl acetate phthalate, hydroxyethyl cellulose phthalate, cellulose acetate tetrahydrophthalate, or Eudragit® L.

U.S. Pat. No. 4,910,021 discloses a targeted delivery system wherein the composition comprises a hard or soft gelatin capsule containing an active ingredient such as insulin and an absorption promoter which is coated with a film forming composition being sufficiently soluble at a pH above 7 as to be capable of permitting the erosion or dissolution of the capsule. The film forming composition is a mixture of Eudragit® L, Eudragit® S, and Eudragit® S at specific ratios to provide solubility above a pH of 7.

U.S. Pat. No. 4,432,966 discloses a compressed tablet with an active agent, coated with a first coating layer comprising a mixture of microcrystalline cellulose and lower alkyl ether of a cellulose film-forming organic polymer such as ethyl cellulose, and a second coating layer selected from cellulose acetylphthalate, hydroxypropyl methylcellulose phthalate, benzophenyl salicylate, cellulose acetosuccinate, copolymers of styrene and of maleic acid, formulated gelatin, salol, keratin, steraric acid, myristic acid, gluten, acrylic and methacrylic resins, and copolymers of maleic acid and phthalic acid derivatives.

U.S. Pat. No. 5,330,759 discloses soft capsules coated with an enteric coating comprising from about 1 to about 20 mg/cm$^2$ of 1:1 copolymer of methacrylic acid and methyl or ethyl acrylate or methyl ethyl methacrylate and a plasticizer.

U.S. Pat. No. 7,704,948 discloses a pharmaceutical composition comprising poloxamer and bisacodyl, wherein the bisacodyl in a single dosage form is coated with an enteric coat, and a protective overcoat is coated on the enteric coat to stabilize the enteric coat from plasticization by the poloxamer, where the enteric coat and the protective overcoat separate poloxamer from the bisacodyl.

WO 1994/018973 discloses a pharmaceutical composition in dosage unit form for per oral administration of bisacodyl to a human or lower animal having a gastrointestinal tract, with a lumen there through, with a small intestine and a colon with a junction there between, comprising: (a) an amount of rapidly-dissolving bisacodyl means; and (b) a delivery means which prevents the release of bisacodyl from the dosage form into the lumen of the gastrointestinal tract during transport of the dosage form through the lumen until the dosage form is near the junction between the small intestine and the colon or in the colon, and which then releases the bisacodyl in the lumen near the junction between the small intestine and the colon or within the colon.

U.S. Pat. No. 5,670,158 discloses a pharmaceutical composition in dosage unit form, for per oral administration of bisacodyl.

U.S. Pat. No. 5,068,110 discloses dosage forms with a high level of enteric coating using aqueous systems in their manufacturer, such as Eudragit® L30D, Aquatic® (cellulose acetate phthalate) and Coat Erie® (polyvinyl acetate phthalate), for improved dissolution stability for storage under high stress conditions. The coating levels disclosed are from 14-24 mg/cm$^2$, of a single layer of one enteric polymer. These dosage forms are delivered to the small intestine as opposed to the colon.

Bisacodyl may also be administered rectally for delivery directly to the colon. U.S. Pat. No. 5,656,290 discloses spherical unit dosage forms containing bisacodyl for colonic delivery to provide laxation in the colon.

C.B. Fleet Company, Incorporated sells a bisacodyl suspension product at a concentration of 0.033% bisacodyl packaged in a 1.25 ounce polyethylene squeeze bottle containing 37 mL of FLEET® Bisacodyl Enema product. The FLEET® Bisacodyl Enema product has an average shelf-life of less than 18 months.

Flexible tubes for packaging foodstuffs and a small portion of pharmaceutically products are known in the art, but such packaging has not been known for use in dispensing for rectal administration.

U.S. Pat. No. 8,377,532 discloses aluminum barrier laminates for use as flexible tube packaging for foodstuffs, such as those manufactured by Huhtamaki, which can be in contact with foodstuffs.

U.S. Patent Application Pub. No. 2012/0010060 discloses a laminate film with at least one barrier layer that may be sterilized. The film layers disclosed include polypropylene with a thickness of 70 μm, aluminum with a thickness of 8

µm, and polyethylene terephthalate with a thickness of 12 µm. A method of making the laminate film is also disclosed.

BRIEF SUMMARY OF THE INVENTION

The invention provides a pharmaceutical composition comprising bisacodyl [4,4'-(pyridin-2-ylmethylene)bis(4,1-phenylene) diacetate], a solvent, and a polymer. In one embodiment, the bisacodyl may be in an amount of about 0.1% (3×) to about 0.5% (15×) by weight of the composition. In another embodiment, the bisacodyl may be in an amount of about 0.10% (3×), 0.15%, 0.20%, 0.25%, 0.30%, 0.31%, 0.32%, 0.33% (10×), 0.34%, or 0.35% by weight of the composition. In many embodiments, the bisacodyl may be a bisacodyl powder with an average particle size of about 10 microns.

In one embodiment, the polymer may be thixotropic. In another embodiment, the polymer may be CARBOPOL ETD 2020 polymer (Acrylates/C10-30 alkyl acrylate cross-polymer). In another embodiment, the polymer may be in an amount of about 0.11% to about 0.15% by weight of the composition. In many embodiments, the polymer may be in an amount of about 0.13% by weight of the composition.

In one embodiment, the solvent may be water, glycerin, or a mixture thereof. In numerous embodiments, the solvent may be a mixture water and glycerin. In numerous embodiments, the water may be in an amount of about 95% to 99% by weight of the composition. In numerous embodiments, the water may be about 96%, 97%, 98%, or 99% by weight of the composition. In numerous embodiments, the glycerin may be in an amount of about 0.8% to 1.2% by weight of the composition. In numerous embodiments, the glycerin may be about 0.93%, 0.94%, 0.95%, 0.96%, 097%, 0.98%, 0.99%, 1.0%, or 1.1% by weight of the composition.

In one embodiment, the density of the composition may be from 0.99 to 1.01.

In one embodiment, the pH may be between 5.0 to 6.8, preferably about 5.6, 5.5, or 5.7. In one embodiment, the composition may comprise a base. In other embodiments, the base may be sodium hydroxide.

In many embodiments, the base may be in an amount of about 0.02-0.05% by weight of the composition, preferably about 0.023% by weight of the composition. In numerous embodiments, the composition may further comprise a buffer in an amount of about 0.01% to about 0.04% by weight of the composition. In many embodiments, the buffer may be in an amount of about 0.01%, 0.02%, 0.03%, or 0.04% by weight of the composition.

In other embodiments, the composition may further comprise a preservative, chelating agent, wetting agent, or a combination thereof.

In many embodiments, the preservative may be methyl paraben, propyl paraben, or a mixture thereof. In many embodiments, the preservative may be a mixture of sodium methyl paraben and sodium propyl paraben in a weight ratio of 0.25%:0.04%, 0.20%: 0.03%, or 0.15%: 0.02%. In many embodiments, the methyl paraben may be in an amount of about 0.1% to about 0.4% by weight of the composition. In many embodiments, the methyl paraben may be in an mount of about 0.15%, 0.18%, 0.19%, 0.20%, 0.21%, or 0.22% by weight of the composition. In many embodiments, the propyl paraben may be in an amount of about 0.01% to about 0.04% by weight of the composition. In many embodiments, the propyl paraben may be in an amount of about 0.01%, 0.02%, 0.03%, or 0.04% by weight of the composition.

In one embodiment, the chelating agent may be disodium EDTA, sodium EDTA, sodium EDTA dihydrate, or a combination thereof. In many embodiments, the chelating agent may be in an amount of about 0.02% to about 0.08% by weight of the composition. In numerous embodiment, the chelating agent may be in an amount of about 0.03%, 0.04%, 0.05%, 0.06%, or 0.07% by weight of the composition.

In many embodiments, the wetting agent may be TRITON X100 (octoxynol 9), Tween 20 (polysorbate 20), Tween 60 (polysorbate 60), Tween 80 (polysorbate 80), PEG 40 hydrogenated castor oil, or a mixture thereof. In many embodiment, the wetting agent may be in an amount of about 0.002% to about 0.010% by weight of the composition. In many embodiments, the wetting agent may be in an amount of about 0.003%, 0.004%, 0.005%, 0.006%, or 0.007% by weight of the composition.

The invention also provides for a method of making the pharmaceutical composition described herein may comprise (a) mixing water and CARBOPOL ETD 2020 polymer (Acrylates/C10-30 alkyl acrylate cross-polymer); (b) add glycerin, TRITON X100 (octoxynol 9), and bisacodyl to the mixture of step (a) and mixing to form a first mixture: (c) heating water to about 65° C.; (d) adding disodium FDTA, methyl paraben, propyl paraben to the heated water of step (c); (e) cooling the mixture of step (d) to about 30° C. to form a second mixture; (f) mixing the first mixture and second mixture to form a third mixture; (g) adding 10% NaOH solution to said third mixture to adjust to final pH of 5.5; and (h) mixing the third mixture to form a bisacodyl composition.

The invention also provides for a method of stimulating a bowel movement comprising administering the pharmaceutical composition described herein to a patient in need thereof.

The invention also provides a composition for stimulating a bowel movement may comprise bisacodyl [4,4'-(pyridin-2-ylmethylene)bis(4,1-phenylene) diacetate], a solvent, a buffer, and a polymer.

The invention also provides for the use of a composition comprising bisacodyl [4,4'-(pyridin-2-ylmethylene)bis(4,1-phenylene) diacetate], a solvent, a buffer, and a polymer, for use in the manufacture of a composition for stimulating a bowel movement.

The invention also provides an enema dispenser comprising a tube comprising a tube opening at a distal end and a closed proximal end; wherein said tube comprises a first laminate layer with an outer surface and an inner surface; a second laminate layer with an outer surface and an inner surface, wherein the outer surface is adjacent to the inner surface of the first laminate layer; a third laminate layer with an outer surface and an inner surface, wherein the outer surface is adjacent to the inner surface of the second laminate layer; a fourth laminate layer with an outer surface and an inner surface, wherein the outer surface is adjacent to the inner surface of the third laminate layer; a fifth laminate layer with an outer surface and an inner surface, wherein the outer surface is adjacent to the inner surface of the fourth laminate layer; a nozzle, attached to the tube at the tube opening, and comprising a distal opening and a tip region, wherein the tip region comprises an opening; a removable sheath on the nozzle: a layer of lubricant in between the nozzle and the removable sheath; and a valve attached to the nozzle.

In another embodiment, the enema dispenser described herein may be filled with 0.33% bisacodyl (10×) formula, wherein the tube used retains a constant volume 3.7 ml after delivery so that a dose of 10 mg of bisacodyl drug was delivered when 6.7 ml filled volume for a 0.33% (10×)

formula (6.7 ml–3.7 ml=3.0 ml) delivered 3.0 ml of a 0.33% (10×) formula=10 mg bisacodyl drug.

In another embodiment, the tube may hold 5.7 mL of a 0.5% (15×) bisacodyl formula delivers a dose of 10 mg of bisacodyl drug when 2.0 mL of 0.5% (15×) formula is delivered into a rectum, and wherein 3.7 mL of 0.5% (15×) formula remains in the tube. In another embodiment, the tube may hold 9.7 mL of a 0.5% (15×) bisacodyl formula and may deliver a dose of 10 mg of bisacodyl drug when 6.0 mL of 0.5% (15×) formula is delivered into a rectum, and wherein 3.7 mL of 5× formula remains in the tube.

In many embodiments, the first laminate layer may be a polypropylene film. In many embodiments, the second laminate layer may be a copolymer extrusion layer. In many embodiments, the third laminate layer may be an aluminum barrier foil. In many embodiments, the fourth laminate layer may be a copolymer extrusion layer. In many embodiments, the fifth laminate layer may be a polypropylene film. In numerous embodiments, the nozzle further may comprise a notch that mates with the removable sheath. In other embodiments, the valve further may comprise a membrane.

In another embodiment, an enema dispenser may comprise a syringe comprising a syringe opening at a distal end wherein the syringe has a fill volume of 5.7 mL for a 0.5% (15×) bisacodyl formula, or a fill volume of 6.7 mL for a 0.33% (10×) formula, or a fill volume of 9.7 mL for a 0.165% (5×) bisacodyl formula; a nozzle, attached to the syringe at the syringe opening, and comprising a distal opening and a tip region; a removable sheath on the nozzle; a layer of lubricant in between the nozzle and the removable sheath; and a valve attached to the nozzle.

In one embodiment, a method of manufacturing a metal laminate tube with a nozzle may comprise the steps of: providing an aluminum barrier laminate tube comprising a distal end and a proximal end, wherein the proximal end is open; wherein the barrier lining in contact with the product is polypropylene; wherein the aluminum barrier laminate tube has a shoulder at the distal end; affixing a nozzle to the distal end of the tube; filling the aluminum barrier laminate tube with a volume of bisacodyl product at the proximal end; heat sealing the proximal end of the tube to form a seal; trimming the excess material located proximal to the seal.

In many embodiments, the nozzle may comprise a distal opening and a tip region. In many embodiments, the nozzle may comprise a valve. In many embodiments, the valve may comprise a membrane. In many embodiments, the nozzle may be affixed to the shoulder at the distal end of the tube. In many embodiments, the nozzle may be affixed to the shoulder at the distal end of the tube by a heat seal. In many embodiments, the filled volume of bisacodyl product (10×) may be between 6.7 mL and 7.3 mL.

In one embodiment, a method of bowel cleansing may comprise removing a protective sheath from an enema dispenser comprising a metal laminate tube with a nozzle and a first volume of bisacodyl composition described herein; inserting the enema dispenser into a rectum; and applying a force to the metal laminate tube sufficient to squeeze a second volume of bisacodyl product through the nozzle and a distal tip of a nozzle into the rectum. In many embodiments, the first volume may be between 6.7 mL to 7.3 mL, and is of a 10× formula bisacodyl composition. In many embodiments, the second volume of bisacodyl composition may be a unit dose. In many embodiments, the unit dose may be between 3.0 to 3.6 mL of a 0.33% (10×) formula bisacodyl composition.

In yet another aspect, the invention provides a method of making a bisacodyl composition, comprising making a first mixture of water and Carbopol ETD 2020 polymer, glycerin, TRITON X100; heating water, adding disodium EDTA, methyl paraben, and propyl paraben to the heated water then cooling it to make a second mixture; creating a third mixture from the first and second mixtures; adding NaOH to adjust the pH of the third mixture, and mixing the third mixture until a bisacodyl composition has formed.

In yet another aspect, the invention provides a method for stimulating a bowel movement by using a composition of bisacodyl [4,4'-(pyridin-2-ylmethylene)bis(4,1-phenylene) diacetate], a solvent, a buffer, and a polymer, and administering it to a patient.

In a further aspect, the invention provides an enema dispenser including a tube made of five laminate layers, a nozzle attached to an opening of the tube, where the nozzle also has an opening at its tip, a removable sheath on the nozzle, a layer of lubricant between the nozzle and the sheath, and a valve attached to the nozzle. The layers are made of polypropylene film, copolymer extrusion, and aluminum barrier foil.

In another aspect, the invention provides a volume of 2.0 mL of a 15× formula of bisacodyl composition to the patient. In yet another aspect, the invention provides a volume of 6.0 mL of 5× formula of bisacodyl composition.

In yet another aspect, the invention provides a syringe to dispense the bisacodyl solution, where the syringe has a volume of 5.7 mL for a 15× formula, 6.7 mL for a 10× formula, and 9.7 mL for a 5× formula, a nozzle with a tip opening attached to the syringe, a removable sheath on the nozzle, a layer of lubricant between the nozzle and the sheath, and a valve attached to the nozzle.

In another aspect, the invention provides a method of manufacturing an enema dispenser, by providing an aluminum barrier laminate tube with an open proximal end, where the innermost layer of the tube, that is in contact with the bisacodyl composition, is polypropylene, attaching a nozzle to the distal end of the tube, filling the tube with a volume of bisacodyl composition at the open proximal end, heat sealing the proximal end to form a seal, and trimming the excess material from the seal.

In another aspect, the invention provides a method of bowel cleansing by removing a protective sheath from the nozzle of a metal laminate tube enema dispenser, inserting the enema dispenser into a rectum, applying a force to the metal laminate tube to squeeze a volume of bisacodyl product through the nozzle and a distal tip of the nozzle into the rectum.

DETAILED DESCRIPTION OF EXEMPLARY EMBODIMENTS

Figure 1:
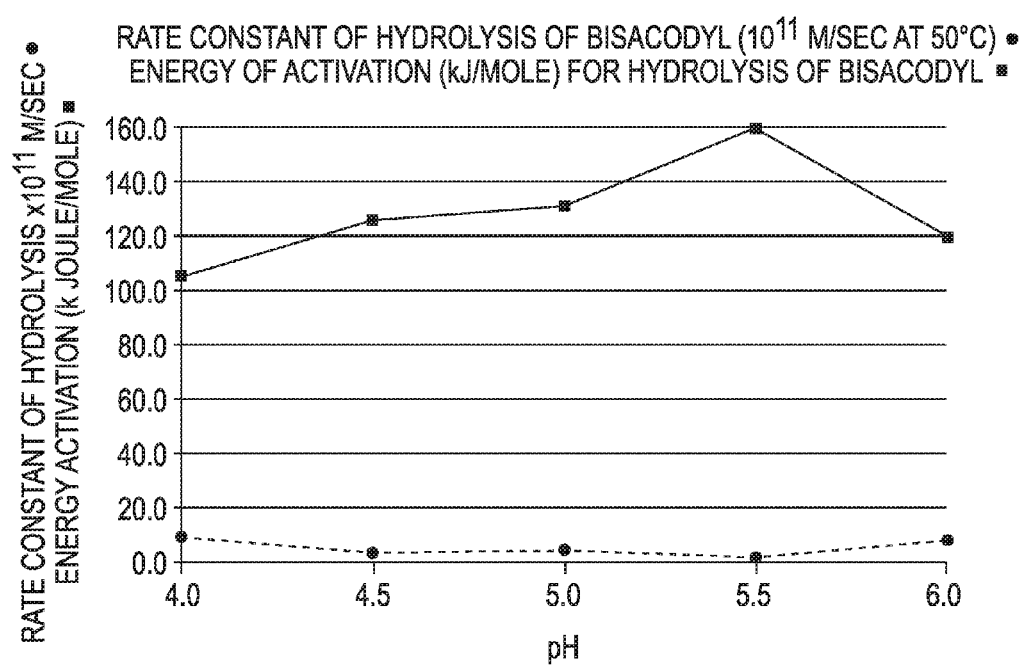
FIG. 1 depicts (A) the change in rate constant of hydrolysis of bisacodyl (●) and (B) the change in energy of activation for its hydrolysis as the pH changes (■).

The present invention relates to bisacodyl compositions, delivery devices, and methods of use as a rectal suppository. The bisacodyl compositions described herein have a shelf life of about 18-24 months.

Both bisacodyl and desacetyl bisacodyl have poor water solubility. Ready-to-use bisacodyl preparations have a short shelf-life (i.e., less than 18 months), can experience settling, and result in waste (e.g., a significant portion of the drug remains in the package). There is a need in the art for a ready-to-use bisacodyl preparation with a longer shelf life and less wasteful apparatus for delivery into the colon.

The product packaging described herein is about 2 times more portable, as compared to the FLEET® Bisacodyl Enema product. The bisacodyl product of this invention delivers 10-fold smaller volume of 3.03 mL with 10× concentration of 0.33% bisacodyl, and this product provides the same delivered dose of 10 mg bisacodyl with less packaging material (2 grams) needed to deliver the product. The inventors surprisingly discovered that manipulation of the solubility properties and improved suspension stability allowed an unexpected improvement in the stability of a bisacodyl laxative product. Further, changes to the packaging allowed for ease of delivery, application, stability (improved shelf life), and single piece construction with a built-in nozzle and lubricant.

The bisacodyl composition described herein may be dispensed rectally from a laminate metal tube fitted with a lubricated nozzle. The patient will experience a bowel movement from 5-20 minutes after the administration of the bisacodyl product described herein.

The bisacodyl composition described herein may also be dispensed rectally from a hand operated syringe fitted with a nozzle.

Process for Development of Bisacodyl Product

A demand exists in the market for a ready-to-use bisacodyl product with a long shelf-life and less waste. The inventors made a number of attempts to make a ready-to-use bisacodyl product with a long shelf-life and less waste via numerous tests using different formulations and carriers. Initial attempts to create a stable suspension were not successful, because the bisacodyl drug has a density of 1.2 g/mL and is not easily suspended.

The molecular formula for bisacodyl is ($C_{22}H_{19}NO_4$), and the molecular weight is 361.39 gram/mole. According to calculation using the software program alogPS[1,2], the aqueous solubility of bisacodyl is 1.23 mg/L. The aqueous molar solubility of bisacodyl at 25° C. is (0.00123 gram/liter)/(361.39 gram/mole)=$3.4 \times 10^{-6}$ M.

The kinetics of the hydrolysis appears to be mixed order, and is predominantly zero order during the shelf life of the product. The average measured pseudo zero order rate constant ($K_o'$) for the hydrolysis of bisacodyl in the 1× (single strength) formulation was calculated using equation 1 to be $2.1 \pm 0.5 \times 10^{-12}$ M/sec. The data was collected from 30 separate experiments with the 1× formulation over a two-year period at an average pH 5.8, and at a storage temperature of 25° C. (298 K).

$$K_o' = (C_o - C)/t \quad \text{Equation 1}$$

where $K_o'$=rate constant for a reaction of pseudo-zero order, $C_0$=concentration of active substance in Moles/liter at time zero, C=concentration of active substance at a later time, t=time in seconds.

The molar concentration of suspended powder in the 1× formula is 0.33 gram/liter 361.39 gram/mole=$9.1 \times 10^{-4}$ M. The molar concentration of suspended powder in the 5× formula is 1.65 gram/liter/361.39 gram/mole–$4.56 \times 10^{-3}$ M. The molar concentration of suspended powder in the 10× formula is 3.3 gram/liter/361.39 gram/mole=$9.1 \times 10^{-3}$ M.

The molar concentration of suspended powder in the 15× formula is 4.95 gram/liter/361.39 gram/mole=$1.37 \times 10^{-2}$ M. The shelf life is the $t_{time}$ it would take for bisacodyl to decrease from the initial concentration by 10%.

$$T_{10} = C_o * 0.1/K_o' \quad \text{equation 2}$$

The initial molar concentration of suspended powder in the 1× formula is 0.33 gram/liter/361.39 gram/mole=$9.1 \times 10^{-4}$ M. The time for 10% decrease in this concentration is calculated to be 16.8 months. Historically, the average shelf life of the 1× formula is seen to be 18 months. The initial molar concentration of suspended powder in the 10× formula is 3.3 gram/liter/361.39 gram/mole=$9.1 \times 10^{-3}$ M. The time for 10% decrease in this concentration is calculated to be 168.0 months.

From the equation 2 shown above, the shelf life can be increased by increasing $C_0$ the amount of active substance at time zero. In practice it is difficult to stabilize a suspension with increased solids content within the parameters of viscosity (<500 cps) and monograph pH range (5.0-6.0). At lower viscosity the yield value of the suspension is inadequate to maintain a stable suspension, and at higher viscosity there is a higher amount of wasted product that is left behind in the container. Within the monograph pH range of 5.0-6.0, the viscosity and yield value of Carbopol ETD 2020 is acceptable. At a pH lower than pH 5.0 the viscosity and yield value of Carbopol ETD 2020 is not acceptable for maintaining a stable suspension.

As shown in FIG. 1, measurements of the pseudo zero order rate constants of hydrolysis of bisacodyl in the 1× formulation (at 50° C. and 80° C.) show little variation in the range of pH from 4.5 to 5.5. The rate of hydrolysis increases below pH 4.5 and the rate of hydrolysis increases above pH 5.5. The Energy of Activation for hydrolysis of bisacodyl is calculated using equation 3 using the pseudo zero order rate constants at 50° C. and 80° C. in the pH range of 4.0-6.0 which are found in Table 1.

$$E_{act} = \ln(k_{80}/k_{50}) * R/(1/323 - 1/353) \quad \text{equation 3}$$

TABLE 1

Pseudo Zero Order Rate constants for hydrolysis of bisacodyl in the 1X formulation at 50° C. and 80° C.

| pH | Rate Constant (M/sec) at 50° C. (323K) | Rate Constant (M/sec) at 80° C. (353K) | $E_{act}$ (kJ/mole) |
|---|---|---|---|
| 4.0 | $8.8 \times 10^{-11}$ | $2.4 \times 10^{-9}$ | 105 |
| 4.5 | $3.1 \times 10^{-11}$ | $1.7 \times 10^{-9}$ | 125 |
| 5.0 | $4.0 \times 10^{-11}$ | $2.5 \times 10^{-9}$ | 131 |

TABLE 1-continued

Pseudo Zero Order Rate constants for hydrolysis of bisacodyl in the 1X formulation at 50° C. and 80° C.

| pH | Rate Constant (M/sec) at 50° C. (323K) | Rate Constant (M/sec) at 80° C. (353K) | $E_{act}$ (kJ/mole) |
|---|---|---|---|
| 5.5 | $2.1 \times 10^{-11}$ | $3.3 \times 10^{-9}$ | 159 |
| 6.0 | $7.8 \times 10^{-11}$ | $3.4 \times 10^{-9}$ | 119 |

Experiments were conducted by adding propylene glycol to the solution. It was thought that adding propylene glycol would reduce the water activity of the mixed solvent and thereby reduce the rate of hydrolysis, instead the rate of hydrolysis increased greatly upon addition of propylene glycol. The increase in the rate of hydrolysis is most likely due to an increase in the solubility of the drug in the water/propylene glycol solution, which exposed more of the drug to hydrolysis.

Several grades of Carbopol were tested to explore the ease of manufacture, and the stability of the suspension over time. The previously marketed product (1×) utilized Carbopol 934P (CAS #9063-87-0), which is cross-linked polyacrylate polymer. Experiments were attempted with varying levels of Ultrez 10NE (CAS #195739-91-4), Carbopol 941 (CAS #600-07-7), and Carbopol ETD 2020 (CAS #176429-87-1, acrylates/C10-30 alkyl acrylate cross-polymer). By comparison with the other thickeners, Carbopol ETD 2020 was shown to be the most efficient thickener. Measurements indicate that Carbopol ETD 2020 generates the greatest yield value with the least amount of thickener being used. Using a controlled stress rheometer, the yield value was measured for the 10× product with 0.13% w/w Carbopol ETD 2020 at various temperatures: 0.12 Pa at 25° C., 0.14 Pa at 20° C., 0.16 Pa at 15° C., 0.18 Pa at 10° C.

Experiments were conducted with various particle sizes ranging from 10 micron (maximum milling), 30 micron (intermediate milling), and 100 micron (unmilled). It was expected that the larger particle size of the 100 micron particle would have a smaller surface area and a slower rate of hydrolysis. Instead, the larger particles sizes of 30 micron and 100 micron were found to settle in the suspension over time, leading to a failure in the assay of the samples at accelerated temperature conditions. This result is explained by the greater yield value required to suspend a larger particle size particle, as shown in the equation 4 for the Estimated Yield Value required to suspend a particle, in units of dyne/cm².

$$\text{Estimated Yield Value} = 4/3 \, R(\rho_{particle} - \rho_{solution})g \quad \text{equation 4}$$

where R=radius of the particle in cm, the difference in density between the particle and the solution: $\rho_{particle} - \rho_{solution} = 0.2$ gram/cm³, acceleration due to gravity, g=980 cm/sec². The required yield value for a 10 micron particle calculated from equation 4 is 0.026 dyne/cm², or 0.0026 Pa. It can been seen from equation 4 that smaller particles (10 micron in 10× formula) require lower yield values for a stable suspension. A solution of 0.13% w/w Carbopol ETD 2020 will supply this yield value.

Other thickeners were evaluated for their ability to suspend bisacodyl powder, such as carboxymethyl cellulose, (Methocel™) methyl cellulose and hydroxypropyl methylcellulose. Suspensions that were made from these thickeners tended to settle over time, leading to a residue of bisacodyl particles on the bottom of the container that resisted suspension after shaking.

The 3× to 10× drug concentration, made stable in a suspension of 0.13% CARBOPOL® ETD 2020, in combination with a smaller dose volume in a laminate metal tube surprisingly led to a shelf life that exceeds 2 years. The high (10×) concentration of the bisacodyl drug was expected to lead to settling (e.g., drug would fall out of suspension, ruining the homogenous distribution of the drug). Also, the bisacodyl drug itself is very water insoluble (e.g., 1.23 mg/L). The inventor surprisingly found that a CARBOPOL® ETD 2020 polymer (C10-30 alkyl acrylate cross polymer) allowed for suspension of bisacodyl in a water-based composition. For example, a composition comprising about 0.11-0.15% CARBOPOL® ETD 2020 polymer (C10-30 alkyl acrylate cross polymer) allowed for a stable suspension of 0.33% bisacodyl.

The solvent for the bisacodyl composition of this invention is water or a water-miscible biocompatible solvent. A polymer is included to make the composition thixotropic, and glycerin is added to bring the specific gravity of the composition close to 1.0 gram/ml. Unit doses of the composition are packaged in squeezable foil tubes, and the polypropylene lining of the laminate tube prevents interaction of the methyl paraben and propyl paraben with the tube wall. The bisacodyl suppository may be in a pH range of 5.0-6.8.

Figure 3:
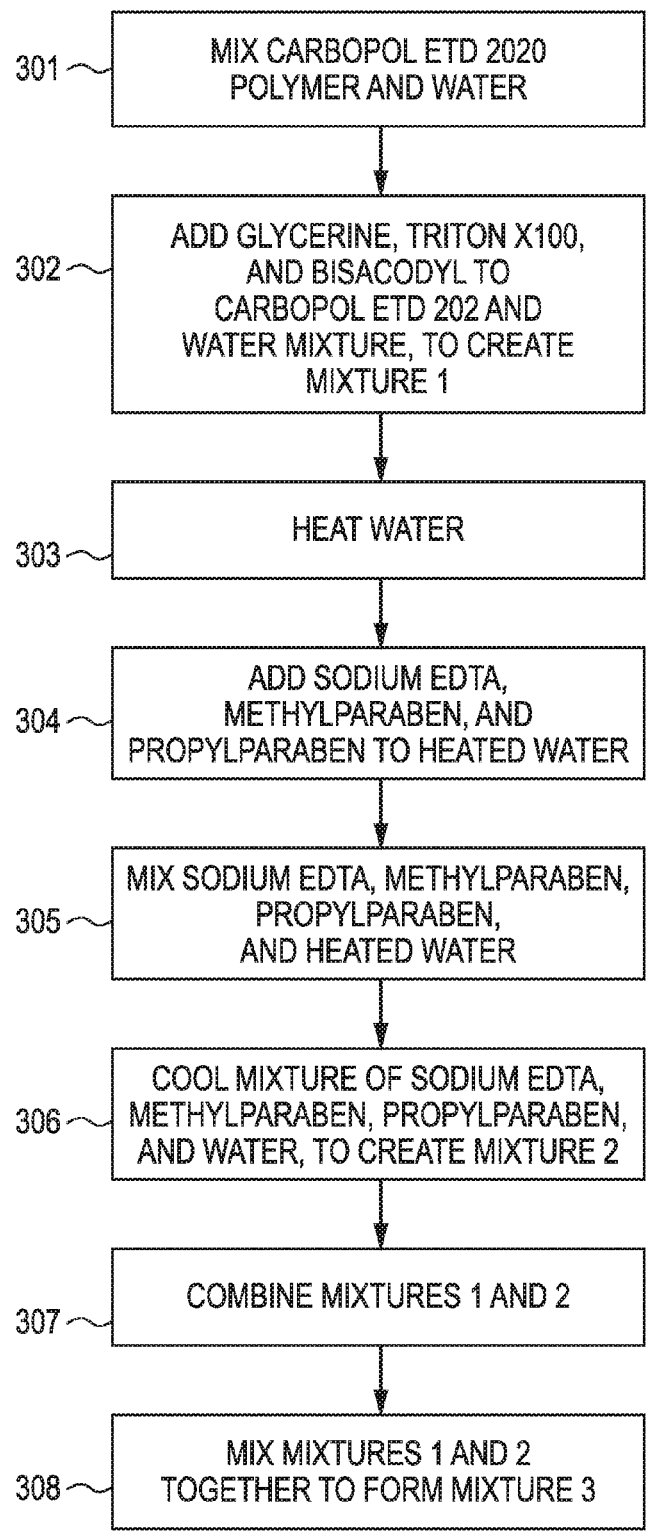
FIG. 3 depicts a method of making a bisacodyl composition.

FIG. 3 depicts the steps taken to form a bisacodyl composition of this invention. In step 1 301, the bisacodyl composition is prepared by mixing water and CARBOPOL ETD 2020 polymer (acrylates/C10-30 alkyl acrylate cross-polymer) together. Step 2 302 is to add glycerine, TRITON X100 (octoxynol 9), and bisacodyl to the water and CARBOPOL ETD 2020 polymer mixture, forming a first mixture. In step 3 303, water is then heated, separately, to about 65° C. Once the water is heated to the proper temperature, sodium EDTA, methyl paraben, and propyl paraben are added to the water in step 4 304; in step 5 305, these ingredients are mixed together and then the mixture is cooled to about 30° C. to form a second mixture in step 6 306. Step 7 307 is to combine the first and second mixtures to form a third mixture. In step 8 308, the combination created in step 7 is mixed together to form a bisacodyl composition. The pH of the bisacodyl composition may be adjusted in a subsequent step to achieve a pH that is consistent with increased stability, as described above.

TABLE 2

Exemplary Bisacodyl Formulation

| Ingredient | Ingredient Function | % w/w |
|---|---|---|
| Water | Solvent | 98.3052% |
| Glycerin | Solvent | 0.9500% |
| Bisacodyl Powder | Laxative | 0.3300% |
| Sodium Hydroxide | pH adjustment | 0.0228% |
| Methyl paraben | preservative | 0.1860% |
| CARBOPOL ETD 2020 (acrylates/C10-30 alkyl acrylate crosspolymer) | Thickener | 0.1300% |
| Disodium EDTA | Chelating Agent | 0.0500% |
| Propyl paraben | Preservative | 0.0210% |
| Triton X100 (octoxynol 9) | wetting agent | 0.0050% |

In an exemplary pharmaceutical composition prepared as described above, the bisacodyl formulation may comprise bisacodyl [4,4'-(pyridin-2-ylmethylene)bis(4,1-phenylene) diacetate], a solvent, a base for pH adjustment, and a polymer. In one example, the composition is provided specifically comprising 0.33% bisacodyl powder (10×) with an average particle size of 10 microns, 0.005% w/w Triton X-100 CG to provide wetting of the powder in a suspension, 0.12%-0.14% w/w Carbopol ETD 2020 to provide a yield value that would suspend the bisacodyl powder, 0.18%-0.20% methyl paraben, 0.01%-0.02% propyl paraben to provide adequate preservation, 0.05%-0.10% EDTA to provide buffering and protection against trace ions that could destabilize the system, 0.9%-1.0% glycerin to reduce the amount of foam generated during mixing and provide some freeze thaw stability, and 0.0228% sodium hydroxide to provide pH adjustment to a desired pH of 5.5.

The bisacodyl formulation may comprise bisacodyl [4,4'-(pyridin-2-ylmethylene)bis(4,1-phenylene) diacetate], one or more solvents, and a polymer, and optionally preservatives, chelating agents, pH adjustment agents, and/or wetting agents.

The bisacodyl may be in an amount of about 0.1% (3×) to about 0.5% (15×) by weight of the composition. Further, the bisacodyl may be in an amount of about 0.10% (3×), 0.15%, 0.20%, 0.25%, 0.30%, 0.31%, 0.32%, 0.33% (10×), 0.34%, or 0.35% by weight of the composition. The bisacodyl may be a bisacodyl powder with an average particle size of about 5-15 microns, preferably about 10 microns.

The polymer may be thixotropic. For example, the polymer may be CARBOPOL ETD 2020 polymer (Acrylates/C10-30 alkyl acrylate cross-polymer) in an amount of about 0.11% to about 0.15% by weight of the composition. The polymer may be in an amount of about 0.13% by weight of the composition.

Water, glycerin, or a mixture thereof may be used as a solvent. For example, a mixture water and glycerin may be used as a solvent. The water may be in an amount of about 95% to 99% by weight of the composition. For example, the water may be about 96%, 97%, 98%, or 99% by weight of the composition. The glycerin may be in an amount of about 0.8% to 1.2% by weight of the composition, preferably about 0.93%, 0.94%, 0.95%, 0.96%, 0.97%, or 0.98% by weight of the composition. The density of the compositions described herein may be from 0.99 to 1.01.

The pH of the compositions described herein may be between 5.0 to 6.8, preferably about 5.6, 5.5, or 5.7. The compositions described herein comprises a base, for example sodium hydroxide in an amount of about 0.02-0.05% by weight of the composition, preferably about 0.023% by weight of the composition. Other pharmaceutically acceptable bases may be used in place or in addition to sodium hydroxide.

The composition may also comprise a buffer which may be in an amount of about 0.01% to about 0.04% by weight of the composition, preferably about 0.01%, 0.02%, 0.03%, or 0.04% by weight of the composition. A suitable buffer may be provided by using sodium acetate to adjust pH to about 5.5, leaving an acetate buffer in the composition.

The compositions described herein may further comprise a preservative, chelating agent, wetting agent, or a combination thereof. For example, methyl paraben, propyl paraben, or a mixture thereof, may be used as preservatives. A mixture of sodium methyl paraben and sodium propyl paraben in a weight ratio of 0.25%:0.04%, 0.20%: 0.03%, or 0.15%: 0.02%. Methyl paraben in an amount of about 0.1% to about 0.4% by weight of the composition may also be used as a preservative. Preferably, the methyl paraben is in an amount of about 0.15%, 0.18%, 0.19%, 0.20%, 0.21%, or 0.22% by weight of the composition. The propyl paraben may be in an amount of about 0.01% to about 0.04% by weight of the composition, preferably about 0.01%, 0.02%, 0.03%, or 0.04% by weight of the composition.

The chelating agent may be disodium EDTA, sodium EDTA, sodium EDTA dihydrate, or a combination thereof, in an amount of about 0.02% to about 0.08% by weight of the composition, preferably about 0.03%, 0.04%, 0.05%, 0.06%, or 0.07% by weight of the composition.

The wetting agent may be TRITON X100 (octoxynol 9), Tween 20 (polysorbate 20), Tween 60 (polysorbate 60), Tween 80 (polysorbate 80), or PEG 40 hydrogenated castor oil.

The wetting agent may be present in an amount of about 0.002% to about 0.010% by weight of the composition, preferably about 0.003%, 0.004%, 0.005%, 0.006%, or 0.007% by weight of the composition.

Delivery Device and Method of Making Delivery Device

Figure 4:
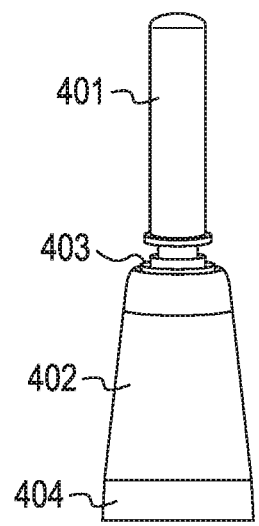
FIG. 4 depicts an exemplary dispensing device having a nozzle with protective sheath and tube.

In certain embodiments, this invention provides a delivery device for the bisacodyl composition which may be a laminate metal tube. The laminate metal tube of the present invention includes a five-layer laminate tube, a nozzle, and a protective sheath on the nozzle. FIG. 4 depicts the assembled laminate tube 402 and nozzle with protective sheath 401. The tube can have a length ranging from 1.75 inches to 2.5 inches, and is capable of holding a volume ranging from 3 mL to 8 mL of bisacodyl composition. In a preferred mode, the tube contains 7.3 mL of the composition. The distal end of the tube has a shoulder 403 to which the nozzle is attached. The attachment of the nozzle to the tube can be done by a heat sealing method.

In another mode of the invention, the tube holds 5.7 mL of a 15× formula of bisacodyl composition. Upon use, a volume of 2.0 mL is dispensed into a rectum, delivering a dose of 10 mg of bisacodyl drug, with 3.7 mL of 15× formula remaining in the tube after use.

In yet another mode of the invention, the tube holds 9.7 mL of a 5× formula of bisacodyl composition. Upon use, a volume of 6.0 mL is dispensed into a rectum, delivering a dose of 10 mg of bisacodyl drug, with 3.7 mL of 15× formula remaining in the tube after use.

A unit dose of the bisacodyl composition is placed into the tube, and then the proximal end 404 of the tube is heat sealed shut. The heat sealing occurs at a temperature range of between 210° C. and 250° C., for a time period of about 1 second. The excess tube material proximal of the heat seal is trimmed off.

Figure 5:
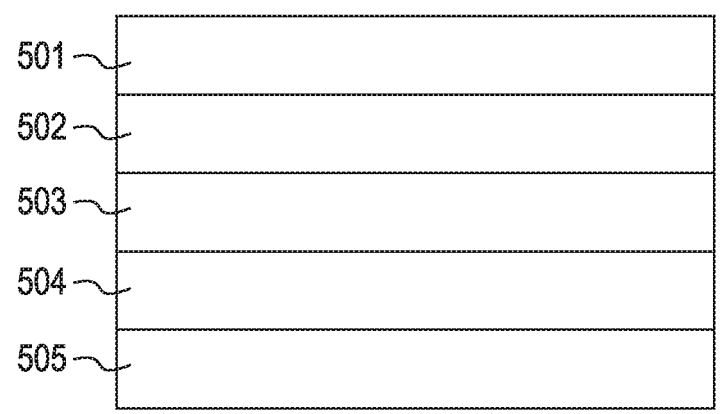
FIG. 5 depicts an exemplary representation of the layers of a tube.

FIG. 5 depicts the layers of the metal laminate tube. The first layer 501 is a polypropylene film, and has a both an inner surface and an outer surface. The second layer 502 is made of a copolymer extrusion and has an inner surface and an outer surface. The inner surface of the first layer is adjacent to the outer surface of the second layer. The third layer 503, which is made of an aluminum barrier foil, has an inner surface and an outer surface. The outer surface of the third layer is adjacent to the inner surface of the second layer. The fourth layer 504 is made of a copolymer extrusion and has an inner surface and an outer surface. The outer surface of the fourth layer is adjacent to the inner surface of the third layer. The fifth layer 505 of the metal laminate tube is a polypropylene film and has both an inner surface and an outer surface. The outer surface of the fifth layer is adjacent to the inner layer of the fourth surface. The inner surface of the fifth layer is in contact with the bisacodyl composition.

Figure 6A:
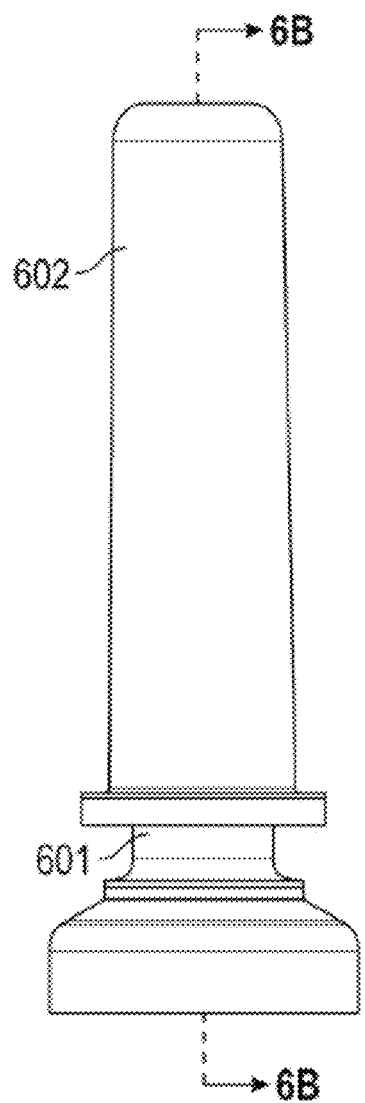
FIGS. 6A and 6B depict a nozzle and a protective sheath for the nozzle.
Figure 6B:
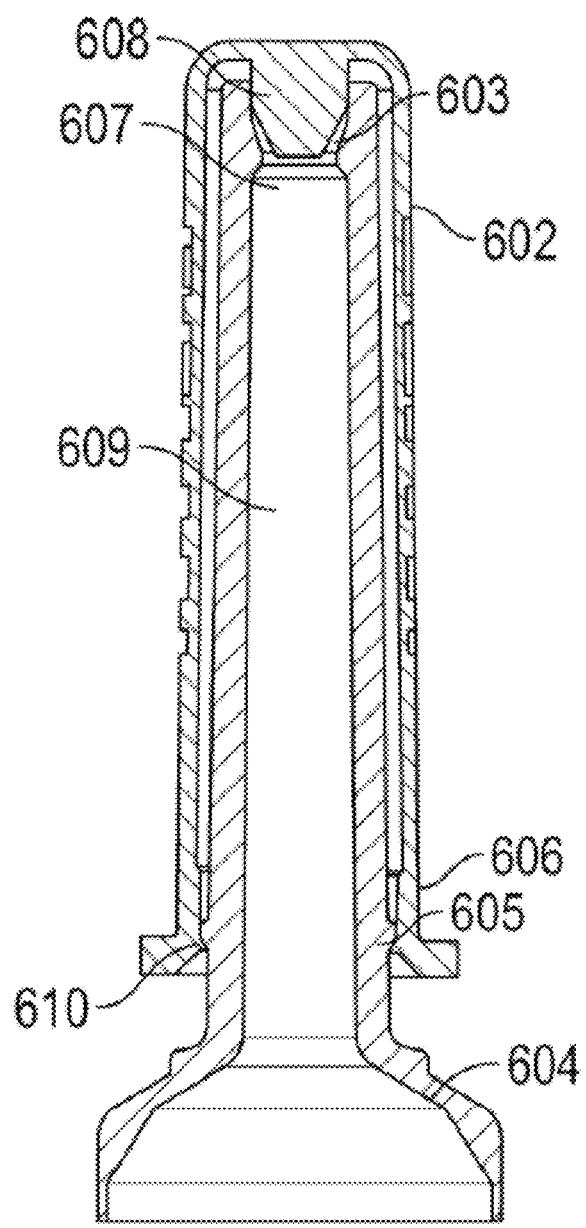

FIG. 6A depicts a nozzle 601 and a protective sheath for the nozzle 602, when the protective sheath is on the nozzle. FIG. 6B depicts a cross-section view of the nozzle and protective sheath of FIG. 6A. The nozzle can be an elongate tube with a distal opening 603 at a distal tip and a shoulder 604 at the proximal end. The nozzle can be 1.7 inches to 2.0 inches long, from its proximal end to its distal end. The neck 609 of the nozzle tube is of a relatively uniform internal diameter. The shoulder is wider than the neck and is attached to the metal laminate tube. The neck of the nozzle can have an external diameter of 0.25 inches to 0.32 inches, and an internal diameter of 0.15 inches to 0.25 inches. The neck preferably has an annular protrusion 605 around the outside of the nozzle to hold the protective sheath 606 in place such that the inner annular-shaped protrusion 610 of the protective sheath is prevented from moving unintentionally in a distal direction by the protrusion 605. The annular protrusion can have an external diameter of about 0.020 to 0.025 inches greater than the diameter of the nozzle neck. The nozzle can be made of a polypropylene material. The nozzle can be made entirely of one piece of polypropylene material. The nozzle also contains a valve 607 which can be located at or near the distal end of the neck or can be located at any position along the length of the neck. The valve may include a membrane. In one mode, the membrane includes a slit, which will permit the passage of liquid under pressure. The protective sheath also has a protrusion 608 at its distal end, that fits into the distal tip of the nozzle and forms a seal when the protective sheath is in place. A lubricated layer (not shown) can be placed in between the nozzle and the protective sheath. The lubricated layer may comprise petrolatum.

Figure 7:
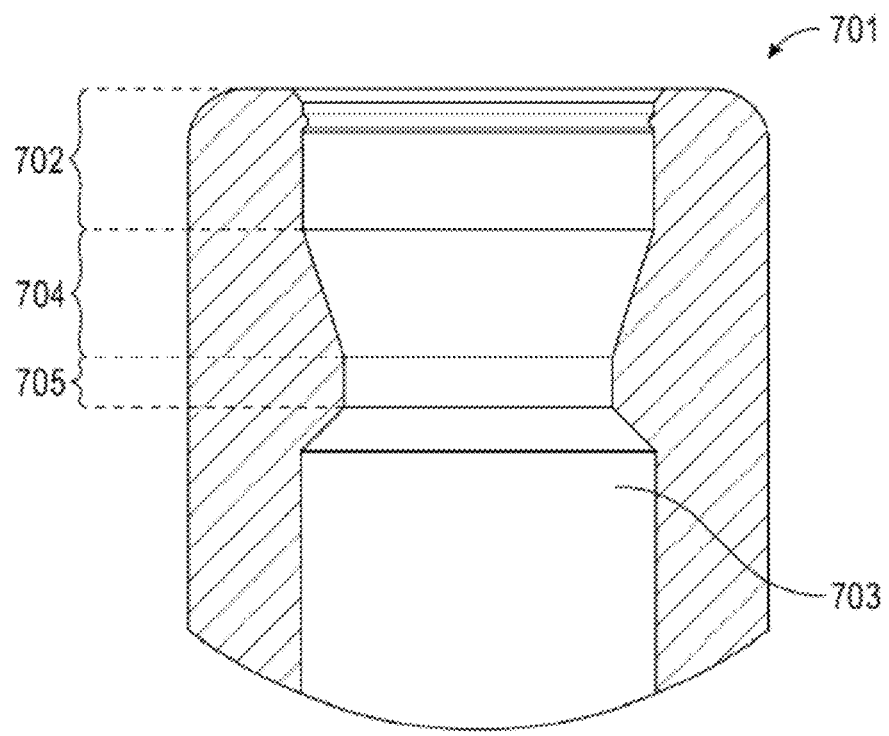
FIG. 7 depicts an exemplary tip of a nozzle.

FIG. 7 is a cross-section view of the distal tip 701 of the nozzle. The distal-most region 702 of the nozzle tip is approximately the same internal diameter as the neck 703 of the nozzle and narrows in the region proximal 704 to distal-most region 702, to the internal diameter of narrow region 705. The distal-most region 702 and the narrowing region 705 are where the proximal end of the protective sheath creates a seal when the protective sheath is on the nozzle.

Figure 8:
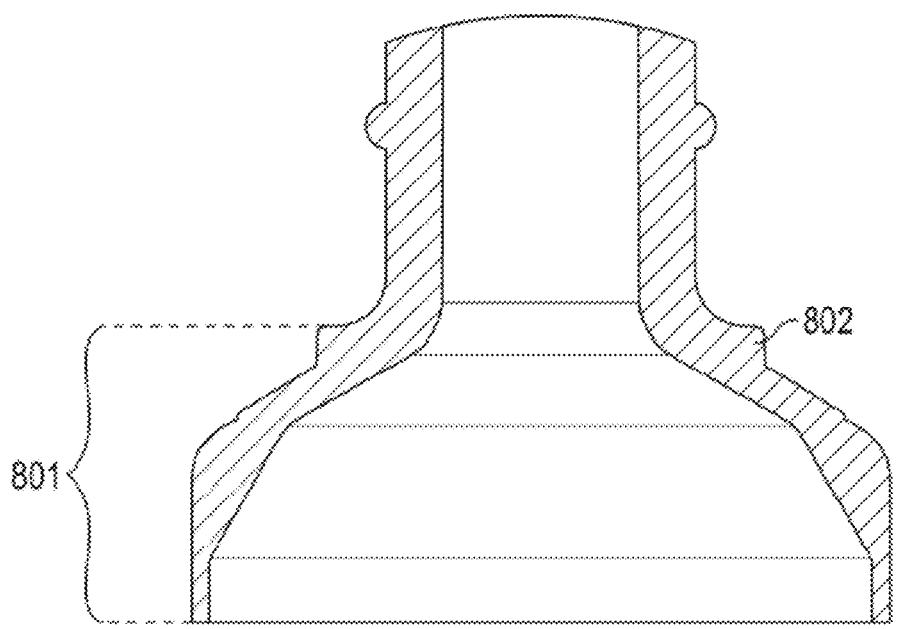
FIG. 8 depicts an exemplary proximal end of a nozzle.

FIG. 8 is a cross-section view of the proximal shoulder 801 of the nozzle. The shoulder also has a step 802. The shoulder can have an external diameter at its widest part, at the most proximal end of the nozzle, of about 0.65 inches to 0.75 inches. The shoulder can have an internal diameter of about 0.55 inches to about 0.70 inches.

In another embodiment, the nozzle, as described above, can be attached to a distal end of a hand-held syringe, where the syringe can hold a volume of 5.0 mL to 8.0 mL of bisacodyl product. A dose delivery study was conducted to determine the quantity of liquid that would be required to deliver a target of 3.0 mL, and 10 mg of bisacodyl in a single squeeze. The amount was determined to be at least 6.7 mL of filled liquid to provide a dose of 3.0 mL.

Figure 9:
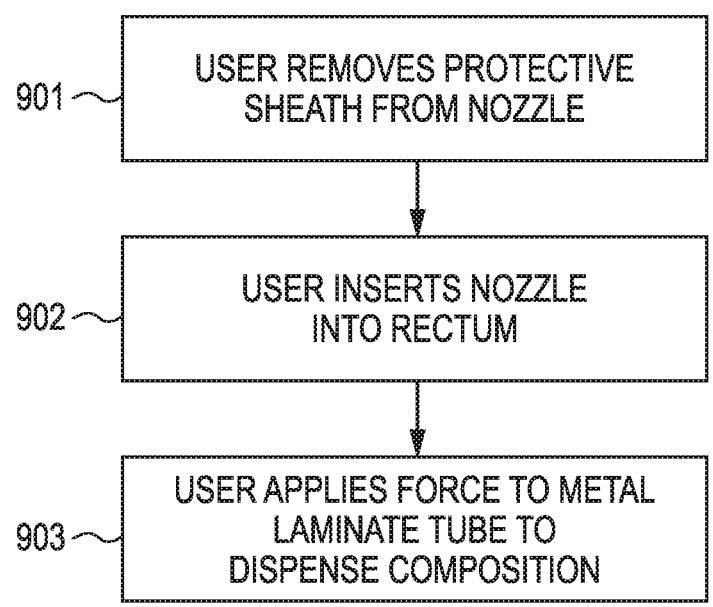
FIG. 9 depicts a method of using an enema dispenser.

FIG. 9 depicts the steps taken in a method of using the enema dispenser with bisacodyl composition. In step 1 901, a user removes the protective sheath. In step 2 902, the user inserts the nozzle of the enema dispenser rectally. In step 3 903, the user applies a force to the metal laminate tube portion of the enema dispenser, causing a unit dose of the bisacodyl product to be dispensed into the rectum.

Further embodiments of the present invention will now be described with reference to the following examples. The examples contained herein are offered by way of illustration and not by any way of limitation.

EXAMPLES

Examples 1

Manufacture of Dispenser Apparatus

In one example of the dispenser, the metal laminate tube of the dispenser is comprised of five layers, from outside to inside, consisting of a polypropylene film layer that is 30 µm thick, a copolymer extrusion layer that is 55 µm thick, an aluminum barrier foil layer that is 12 µm thick, another copolymer extrusion layer that is 55 µm thick, and another polypropylene film layer that is 30 µm thick. In this embodiment, the material of the tube has a total thickness of 182 µm. The tube in this example is supplied with an open bottom end. A nozzle that has a membrane valve with a slit in it is secured to the shoulder at the proximal end of the tube by heat sealing the pieces together, petrolatum is applied to the nozzle, and a protective sheath is fitted onto the nozzle.

Example 2

Manufacture of Bisacodyl Composition

A bisacodyl composition is prepared by mixing water and CARBOPOL ETD 2020 polymer (acrylates/C10-30 alkyl acrylate cross-polymer) together. Glycerin, TRITON X100 (octoxynol 9), and bisacodyl are added to the water and CARBOPOL ETD 2020 polymer mixture to form a first mixture. Water is then heated to about 65° C., and then sodium EDTA, methyl paraben, and propyl paraben are added to the water and mixed together. This mixture with EDTA is then cooled to about 30° C. to form a second mixture. The first and second mixtures are combined and mixed to create a third mixture which is a bisacodyl composition. In the bisacodyl composition, the water has a percent weight of 98.3052%; glycerin has a percent weight of 0.9500%; bisacodyl powder has a percent weight of 0.3300%, sodium hydroxide has a percent weight of 0.0228%; methyl paraben has a percent weight of 0.1860%; CARBOPOL ETD 2020 has a percent weight of 0.1300%; disodium EDTA has a percent weight of 0.0500%; propyl paraben has a percent weight of 0.0210%; and Triton X100 has a percent weight of 0.0050%.

Example 3

Filling Dispensing Apparatus

In this example of loading the dispenser, the metal laminate tube with a nozzle and protective sheath on one end and an opening at the other end, is loaded with bisacodyl composition and then further prepared to produce a saleable product. The metal laminate tube is filled from the open end with 7.3 mL of a bisacodyl composition. The open end of the tube is then heat sealed shut for 1 second at a temperature of 250° C., and the excess tube material is trimmed from the tube.

Example 4

Administration of Bisacodyl Composition

In this example, the enema is administered by removing the protective sheath, inserting it into a rectum, and applying a compression force to the metal laminate tube. Of the 7.3 mL of bisacodyl composition in the tube, a unit dose volume of 3 mL is dispensed through the valve and distal opening of the nozzle, and injected into the rectum. The remaining volume of bisacodyl composition remains in the tube and will be discarded.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

While the foregoing invention has been described in connection with this preferred embodiment, it is not to be limited thereby but is to be limited solely by the scope of the claims which follow.

Example 5

Manufacture of Liquid Suppository

Figure 2:
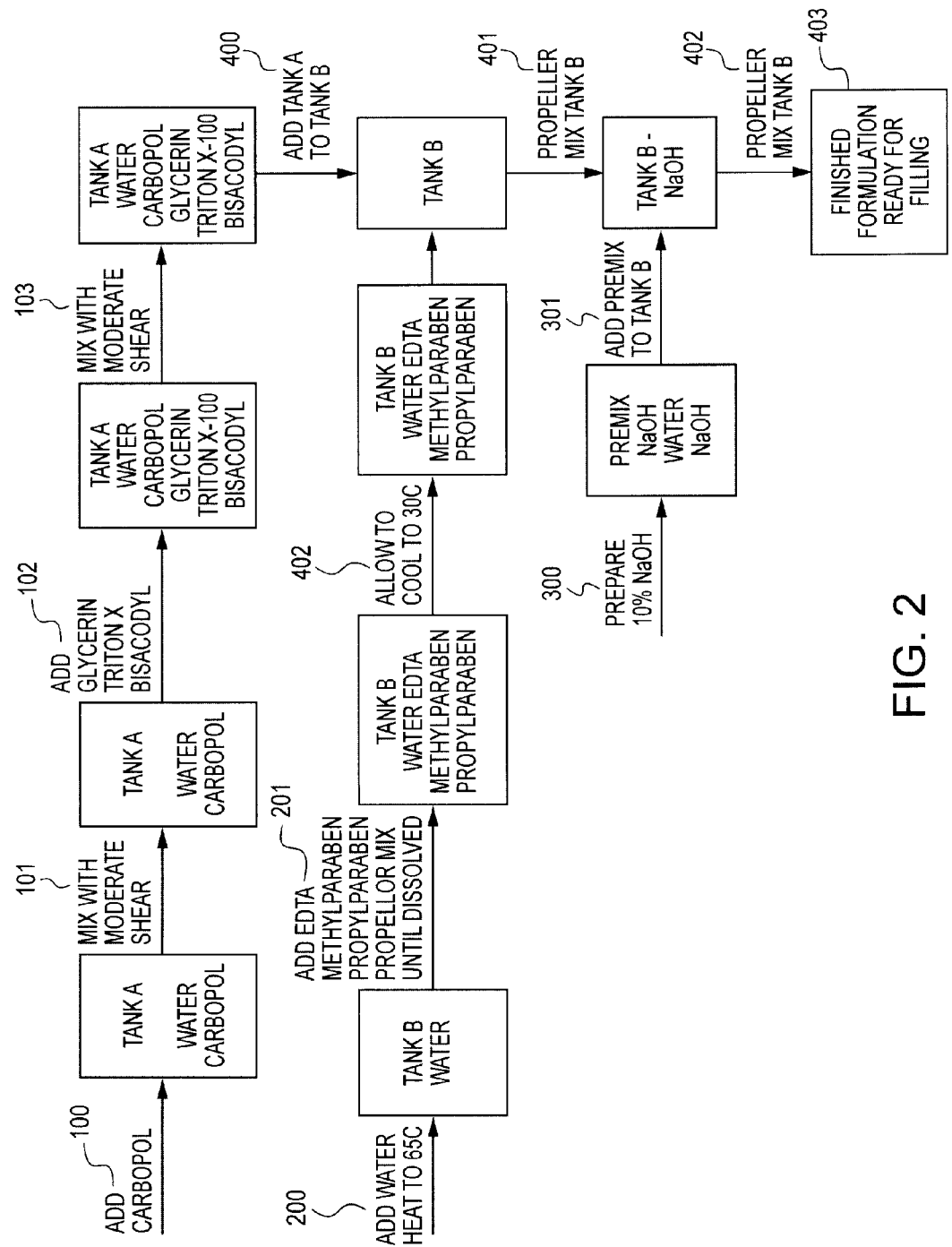
FIG. 2 depicts an exemplary flow chart of manufacturing bisacodyl compositions.

FIG. 2 illustrates a method of making a liquid suppository. Water and CARBOPOL® ETD 2020 are added to Tank A at 100. The water and the CARBOPOL® ETD 2020 are mixed with moderate shear at 101. Glycerin, TRITON™ X-100 and bisacodyl are added to the water and CARBOPOL® ETD 2020 in Tank A at 102. The water. CARBOPOL® ETD 2020, glycerin, TRITON™ X-100 and bisacodyl are mixed with moderate shear at 103 to form a first mixture. Water is added to Tank B and heated to 65° C. at 200. EDTA, methyl paraben and propyl paraben are added to the water in Tank B and propeller mixed until dissolved at 201. The water, EDTA, methyl paraben and propyl paraben are allowed to cool to 30° C. at 402 to form a second mixture. The first mixture is added to the second mixture in Tank B at 400 to form a third mixture. The third mixture is propeller mixed at 401. A 10% sodium hydroxide solution is added to water at 300 to form a Premix in a separate tank. The premix is added to the third mixture at 301 to form a fourth mixture. The fourth mixture is propeller mixed at 402 to form a finished formulation at 403.

Example 6

Comparative Shelf Life Test

Figure 10A:
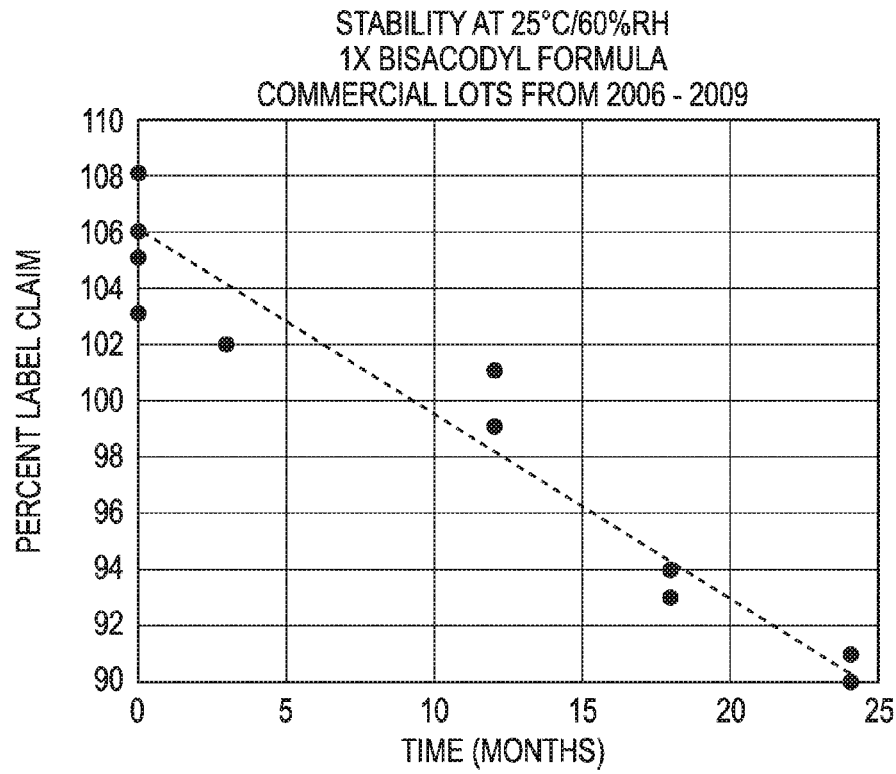
FIGS. 10A and 10B depict the change in the percent of label claim of bisacodyl formula in commercial lots over time.
Figure 10B:
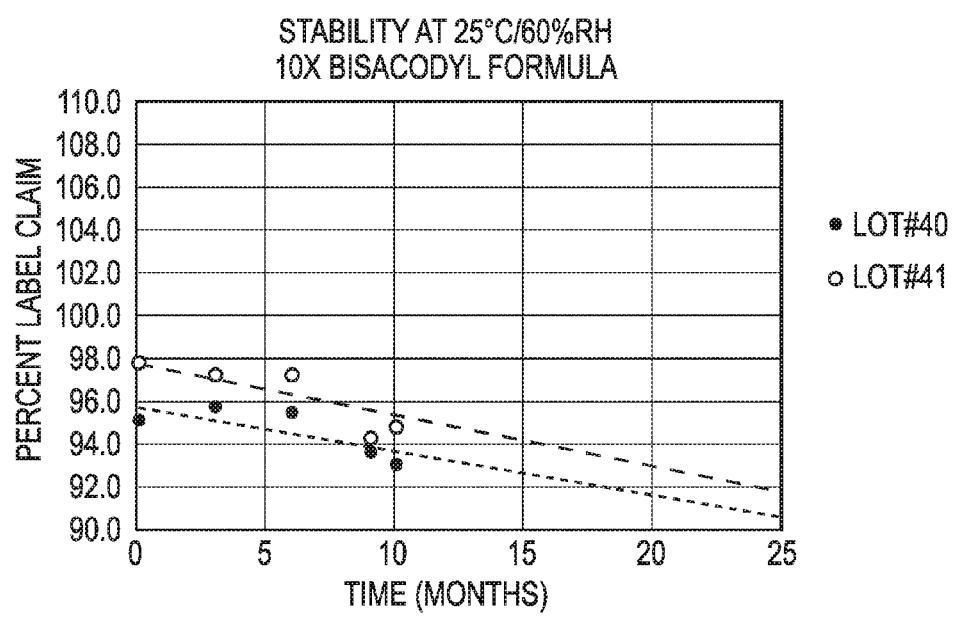

The shelf life of a 0.033% bisacodyl liquid suppository was compared to the shelf life of a 0.33% bisacodyl liquid suppository. The shelf life of a liquid suppository is defined as the time when the initial concentration of the liquid suppository has been reduced by 10%. Shelf life was determined by measuring the initial concentration of bisacodyl in the liquid suppository and measuring the concentration of bisacodyl in the liquid suppository at various time intervals. The liquid suppositories were stored at 25° C. and 60% relative humidity. FIG. 10A illustrates a graph of the shelf life data for multiple commercial lots of a 0.033% bisacodyl liquid suppository. The initial concentration of the 0.033% bisacodyl liquid suppository was reduced by 10% at 15 months, indicating a shelf life of 15 months. The initial concentration shown in FIG. 10A includes percent label claims that are greater than 100, which indicates that a liquid suppository was formulated to include a greater concentration of active ingredient than the concentration shown on the label, known as an overage. FIG. 10B illustrates a graph of the shelf life data for two lots of a 0.33% bisacodyl liquid suppository. The initial concentration of the 0.33% bisacodyl liquid suppository was reduced by less than 6% at 24 months, indicating a shelf life of at least 24 months. The results indicate that the 0.33% bisacodyl liquid suppository has a shelf life that is at least 1.6 times greater than the shelf life of the 0.033% bisacodyl liquid suppository.

Example 7

Rheology Tests of Bisacodyl Liquid Suppository

Figure 11A:
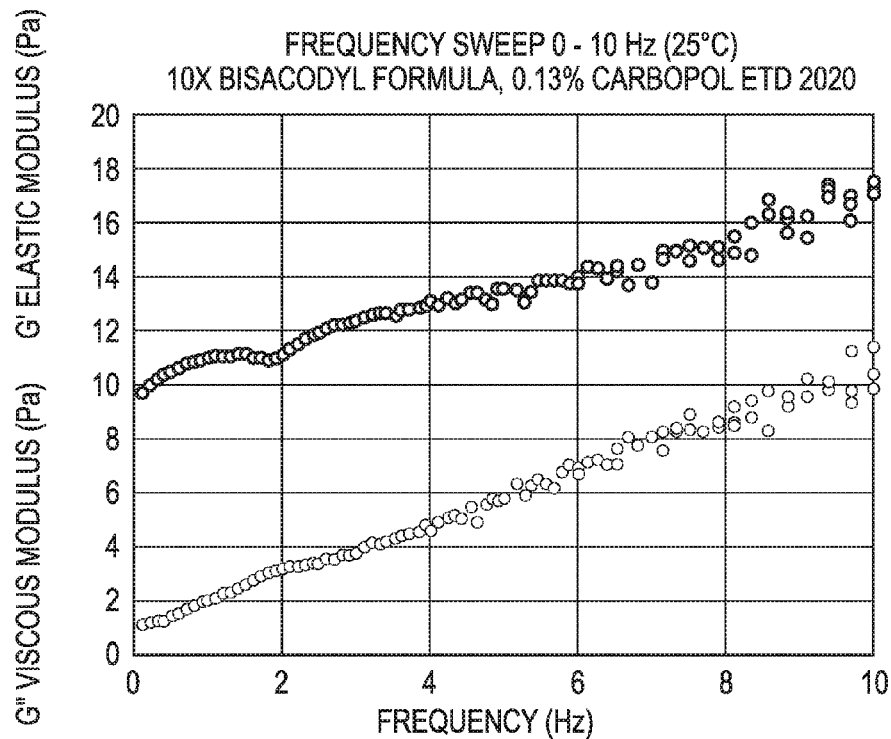
FIG. 11A illustrates a graph of the elastic modulus (G') and the viscous modulus (G") in Pascals at various frequencies.
Figure 11B:
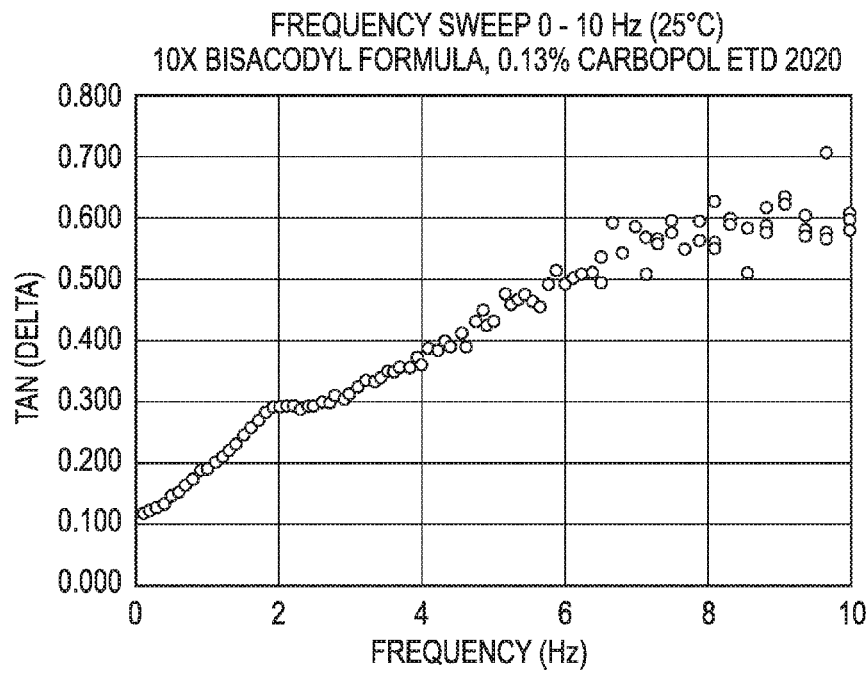
FIG. 11B depicts the change of Tan(Delta), which is the ratio of G" over G', as frequency changes.
Figure 11C:
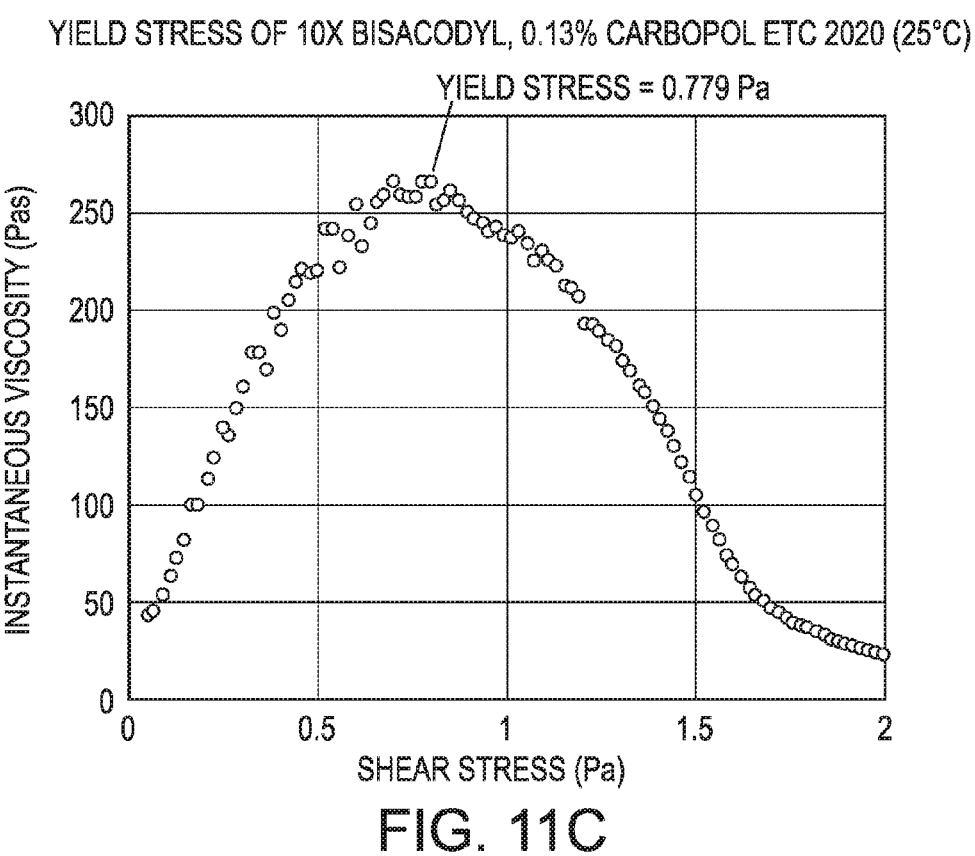
FIG. 11C depicts the change in instantaneous viscosity as shear stress changes.

A 0.33% bisacodyl liquid suppository including 0.13% CARBOPOL® ETD 2020 was prepared. A frequency sweep experiment was carried out on the liquid suppository between 0-10 Hz at 25° C. using a BOHLIN® rheometer. FIG. 11A illustrates a graph of the elastic modulus (G') and the viscous modulus (G") in Pascals at various frequencies. G" does not cross G", indicating that the suppository is a well-structured gelled system with strongly associated particles where sedimentation is unlikely to occur. The elastic modulus was greater than the viscous modulus over the range of frequencies, indicating that the suppository was a stable suspension with particles that strongly interact with each other. FIG. 11B illustrates a graph of Tan (Delta) at various frequencies. Tan (Delta) is defined as G"/G' (viscous modulus/elastic modulus). Tan (Delta) was less than 1 over the range of frequencies, indicating that the suspended particles strongly interact with each other and the suspension is stable. FIG. 11C illustrates a graph of the yield stress of the liquid suppository. The instantaneous viscosity was measured at a shear stress between 0-2 Pascals. The liquid suppository had a yield stress of 0.779 Pa. The yield stress test was repeated for other liquid suppositories including different types of CARBOPOL® polymers at the same concentration. The other liquid suppositories had a yield stress that was less than 0.779 Pascals. The yield stress tests suggest that CARBOPOL® ETD 2020 provides greater stability than other CARBOPOL® polymers in an otherwise identical suppository formulation.

Example 8

Comparison of 0.033% Bisacodyl Liquid Suppository and 0.33% Bisacodyl Liquid Suppository An existing commercially-available bisacodyl liquid suppository was compared to a bisacodyl liquid suppository according to the present invention. The results are shown below in Table 3:

TABLE 3

Comparison of 0.033% bisacodyl liquid suppository and 0.33% bisacodyl liquid suppository

| | | |
|---|---|---|
| Biscadoyl concentration | 0.033% | 0.33% |
| Product form | 1.25 oz bottle | 7 g multi-layered tube |
| Packaging weight | 10 g | 2 g |
| Packaging volume | 178.85 $cm^3$ | 90 $cm^3$ |
| Volume of bisacodyl solution | 37 mL | 3.03 mL |
| Shelf life | At most 18 months | At least 24 months |

The 0.033% bisacodyl liquid suppository and the 0.33% bisacodyl liquid suppository both deliver a 10 mg dose of bisacodyl. The results above show that the 0.33% bisacodyl liquid suppository delivers this dose in a smaller, lighter package and has a longer shelf life. The 0.33% bisacodyl liquid suppository will be less expensive to produce and ship, as well as lighter and more portable for a user.

As used in this application, the term "particle size" means the average diameter of the image of the particle as viewed by electron microscopy unless otherwise stated. The term "average particle size" means the average of the particle sizes of a collection of particles.

What is claimed is:

1. An enema, comprising:
    bisacodyl,
    acrylates/C10-30 alkyl acrylate cross-polymer,
    optionally, a solvent,
    optionally, a pH adjuster,
    optionally, a buffer,
    optionally, a preservative,
    optionally, a chelating agent, and
    optionally, a wetting agent,
    wherein the bisacodyl is present in an amount of at least 0.1% by weight, and
    the enema is packaged in a laminate metal tube.

2. The enema of claim 1, consisting essentially of:
    bisacodyl,
    acrylates/C10-30 alkyl acrylate cross-polymer,
    optionally, a solvent,
    optionally, a pH adjuster,
    optionally, a buffer,
    optionally, a preservative,
    optionally, a chelating agent, and
    optionally, a wetting agent.

3. The enema of claim 1, wherein the bisacodyl is present in an amount of 0.1-0.5% by weight.

4. The enema of claim 1, wherein the acrylates/C10-30 alkyl acrylate cross-polymer is present in an amount of 0.11-0.15% by weight.

5. The enema of claim 1, further comprising the solvent,
    wherein the solvent is present in an amount of 95-99% by weight, and
    the solvent comprises at least one member selected from the group consisting of water and glycerin.

6. The enema of claim 1, further comprising the pH adjuster,
    wherein the pH adjuster is present in an amount of 0.02-0.05% by weight.

7. The enema of claim 1, further comprising the buffer,
    wherein the buffer is present in an amount of 0.01-0.04% by weight.

8. The enema of claim 1, further comprising the preservative,
    wherein the preservative is present in an amount of 0.01-0.4% by weight, and
    the preservative comprises at least one member selected from the group consisting of methyl paraben and propyl paraben.

9. The enema of claim 1, further comprising the chelating agent,
    wherein the chelating agent is present in an amount of 0.02-0.08% by weight.

10. The enema of claim 1, further comprising the wetting agent,
    wherein the wetting agent is present in an amount of 0.002-0.010% by weight, and
    the wetting agent comprises at least one member selected from the group consisting of octoxynol 9, polysorbate 20, polysorbate 60, polysorbate 80 and PEG 40 hydrogenated castor oil.

11. The enema of claim 1, wherein the enema is formulated as a suspension.

12. The enema of claim 1, wherein the enema has a pH of 5.0-6.8.

13. The enema of claim 1, wherein the bisacodyl comprises bisacodyl particles having an average particle size of 5-15 µm.

14. The enema of claim 1, wherein the bisacodyl is present in an amount of 0.1-0.5% by weight,
    the acrylates/C10-30 alkyl acrylate cross-polymer is present in an amount of 0.11-0.15% by weight,
    the solvent comprises water and glycerin in an amount of 95-99% by weight,
    the preservative comprises methyl paraben and propyl paraben in an amount of 0.01-0.4% by weight,
    the chelating agent comprises EDTA in an amount of 0.02-0.08% by weight, and
    the wetting agent comprises octoxynol 9 in an amount of 0.002-0.010% by weight.

15. The enema of claim 2, wherein the bisacodyl is present in an amount of 0.1-0.5% by weight,
    the acrylates/C10-30 alkyl acrylate cross-polymer is present in an amount of 0.11-0.15% by weight,
    the solvent comprises water and glycerin in an amount of 95-99% by weight,
    the preservative comprises methyl paraben and propyl paraben in an amount of 0.01-0.4% by weight,
    the chelating agent comprises EDTA in an amount of 0.02-0.08% by weight, and
    the wetting agent comprises octoxynol 9 in an amount of 0.002-0.010% by weight.

16. The enema of claim 1, wherein the bisacodyl is present in an amount of at least 0.30% by weight.

17. The enema of claim 1, wherein the enema has a shelf life greater than 18 months.

18. The enema of claim 1, wherein the enema has a shelf life greater than 24 months.

19. The enema of claim 1, wherein the laminate metal tube is capable of holding 3-8 mL of enema.

20. The enema of claim 1, wherein the laminate metal tube comprises a nozzle, and
    a protective sheath, on the nozzle.

* * * * *